United States Patent

Kudo et al.

[11] Patent Number: 5,840,952
[45] Date of Patent: Nov. 24, 1998

[54] METHOD OF MANUFACTURING 3-MERCAPTOPROPYLALKOXY SILANE

[75] Inventors: Muneo Kudo; Hideyoshi Yanagisawa; Shoji Ichinohe; Akira Yamamoto, all of Gunma-ken; Satoru Beppu, Joetsu; Hiroyuki Iwaki, Niigata-ken; Satoshi Sekizawa, Takaoka, all of Japan

[73] Assignee: Shin-Etsu Chemical Co., Ltd., Tokyo, Japan

[21] Appl. No.: 741,684

[22] Filed: Oct. 31, 1996

[30] Foreign Application Priority Data

Nov. 2, 1995 [JP] Japan .................................. 7-309895

[51] Int. Cl.⁶ .................................. C07F 7/08; C07F 7/18
[52] U.S. Cl. .............................................................. 556/429
[58] Field of Search ............................................. 556/429

[56] References Cited

U.S. PATENT DOCUMENTS

| | | |
|---|---|---|
| 3,532,733 | 10/1970 | Lee .......................................... 556/429 |
| 3,627,802 | 12/1971 | Lee .......................................... 556/429 |
| 4,082,790 | 4/1978 | Speier ...................................... 556/429 |
| 4,556,724 | 12/1985 | Seiler et al. ............................ 556/429 |
| 5,107,009 | 4/1992 | Rauleder et al. ....................... 556/429 |

*Primary Examiner*—Paul F. Shaver
*Attorney, Agent, or Firm*—Townsend & Banta

[57] ABSTRACT

After reacting sodium sulfide anhydride and hydrogen sulfide, 3-halopropylalkoxy silane represented by the general formula $$X(CH_2)_3Si(OR)_aR_{3-a} \qquad (I)$$

is added reacted, wherein X denotes Cl or Br; R denotes a methyl, ethyl or propyl group wherein R's can be all identical or different from each other; and "a" denotes an integer 1, 2 or 3.

7 Claims, No Drawings

METHOD OF MANUFACTURING 3-MERCAPTOPROPYLALKOXY SILANE

RELATED APPLICATIONS

This application claims the priority of Japanese Patent application No.7-309895 filed on Nov. 2, 1995, which is incorporeted herein by reference.

BACKGROUND OF THE INVENTION

1. Field of the Invention

This invention relates to a method of manufacturing 3-mercaptopropylalkoxy silane, which is useful as a silane coupling agent.

2. The Prior Art

Conventionally, the reaction between haloalkylalkoxy silane and thio-urea in the presence of ammonia has been known as a method of manufacturing mercaptopropylalkoxy silane (Japanese examined patent publication Tokko Sho 50-7587).

However, this reaction has a problem in that it produces as a by-product guanidine hydrochloride, which is bulky and difficult waste to treat.

An alternative method in which haloallkylalkoxy silane is reacted with hydrogen sulfide in the presence of an amine (or a derivative) (Tokko Sho 60-2312) is also known. However, this reaction has a problem in that it has to be carried out under a high pressure of 16 kg/cm$^2$.

An addition reaction of hydrogen sulfide to alkenylalkoxy silane is also known (U.S. Pat. No. 3,890,213). However, this reaction has a problem in that the produced mercaptoalkylalkoxy silane again adds on to alkenylalkoxy silane, the raw material, resulting in a large amount of sulfide compound by-products.

Furthermore, a method in which sodium methoxide and hydrogen sulfide are reacted, followed by reacting haloalkylalkoxy silane, is known as well. Examples of this method include a method in which the reaction (s) is carried out at room temperature in a methanol solution of sodium hydrogensulfid (U.K. patent No. 11022251) and a method in which sodium hydrogensulfide is dissolved in a non-polar non-protonic solvent, typically dimethylformamide, and the reaction(s) is carried out at atmospheric pressure (Japanese unexamined patent publication Tokkai Hei 4-261188). However, there is a problem in that the reaction between sodium methoxide and hydrogen sulfide produces sodium sulfide as a by-product, and this leads to a large amount of by-product sulfide compounds unless it is removed. Removing it is not an easy process.

Also, U.K. patent No. 1102251 has shortcomings which cannot be ignored from a practical point of view, including the requirement of an extremely long reaction time, i.e. 4 days, and a low conversion ratio. Tokkai Hei 4-261188 has shortcomings including use of a solvent with a high boiling point which requires a distillation tower with a relatively high number of theoretical plates for distillation separation of the product and adds to the cost of manufacturing mercapto silane because of the higher energy required for the separation. Also, because of the high dissolving power of the solvent the salt which is not separated before the distillation is transferred to the distillation still solution and lowers the distillation recovery ratio of the product.

Furthermore, a common shortcoming of these methods is that the yield is only about 80%. This means not only an economic disadvantage but also a consierable cost to treat hazardous substances contained in the raw materials and by-products remaining after the reaction. Because of this, these methods are not satisfactory for industrial mass production.

In order to eliminate the shortcomings of these prior art methods and carry out low-cost industrial mass production, it is necessary to use a cheap raw material(s) and achieve a high conversion ratio in a short time. That is, it is necessary to significantly increase the conversion ratio from the raw material, 3-chloropropylalkoxy silane, to the target product, 3-mercaptopropylalkoxy silane and control the generation of by-product components other than the target product to reduce the load of the after treatment, and complete the production in a short amount of time using a simple production apparatus.

BRIEF SUMMARY OF THE INVENTION

The object of the present invention is to provide a new manufacturing method which gives a high yield of 3-mercaptopropylalkoxy silane under mild conditions, suppresses the production of the by-product sulfide compounds and, at the same time, produces by-product salts for which waste treatment is not difficult.

The present invention provides a method of manufacturing 3-mercaptopropylalkoxy silane wherein, after reacting sodium sulfide anhydride and hydrogen sulfide, 3-halopropylalkoxy silane represented by the general formula $$X(CH_2)_3Si(OR)_aR_{3-a} \qquad (I)$$

is added and reacted, wherein X denotes Cl or Br; R denotes a methyl, ethyl or propyl group wherein R's can be all identical or different from each other; and "a" denotes an integer 1, 2 or 3.

Also, the present invention provides a method of manufacturing 3-mercaptopropylalkoxy silane wherein a hydrogensulfide of alkali metal and 3-halopropylalkoxy silane represented by the general formula $$X(CH_2)_3Si(OR)_aR_{3-a} \qquad (I)$$

are reacted under airtight and pressurized conditions in the presence of hydrogen sulfide, where X denotes Cl or Br; R denotes a methyl, ethyl or propyl group wherein R's can be all identical or different from each other; and "a" denotes an integer 1, 2 or 3.

DETAILED DESCRIPTION

The present invention is described in detail below.

The 3-halopropylalkoxy silane used in the present invention is represented by the general formula $$X(CH_2)_3Si(OR)_aR_{3-a} \qquad (I)$$

wherein X denotes Cl or B; R denotes a methyl, ethyl or propyl group wherein R's can be all identical or different from each other; and "a" denotes an integer 1, 2 or 3. The specific examples include Cl(CH$_2$)$_3$Si(OMe)$_3$, Br (CH$_2$)$_3$Si(OMe)$_3$, Cl(CH$_2$)$_3$Si(OMe)$_2$Me, Cl(CH$_2$)$_3$Si(OEt)$_3$, Cl(CH$_2$)$_3$Si(OPr)$_2$Me and Cl(CH$_2$)$_3$Si(OMe) Me$_2$.

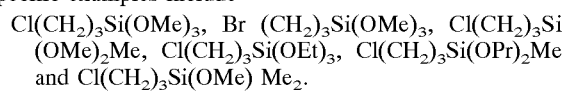

For the silane coupling agent, dialkoxy silane or trialkoxy silane with a=2 or 3 is preferable, and trialkoxy silane is particularly preferable. R is preferably a methyl group or ethyl group because of reactivity and ease of obtaining the raw material. A methyl group is particularly preferable.

For said 3-halopropylalkoxy silane, $Cl(CH_2)_3Si(OMe)_3$ or $Br(CH_2)_3Si(OMe)_3$ is the most preferable, and $HS(CH_2)_3Si(OMe)_3$ obtained from it is useful.

[The manufacturing method in which sodium sulfide anhydride and hydrogen sulfide are reacted and then 3-halopropylalkoxy silane is added and reacted.]

This reaction is represented by $$½ Na_2S + ½ H_2S \rightarrow NaSH \qquad (1)$$

and $$NaSH + X(CH_2)_3Si(OR)_aR_{3-1} \rightarrow HS(CH_2)_3Si(OR)_3R_{3-a} + NaX. \qquad (2)$$

Since reaction (1) has few by-products, production of the by-product sulfide can be suppressed.

The first step, that is, the reaction between sodium sulfide anhydride and hydrogen sulfide, is described below.

Hydrogen sulfide, whose amount is preferably 1–2 equivalents, more preferably 1.0–1.4 equivalents, of sodium sulfide anhydride, is blown in, and the reaction is carried out preferably at 20°–100° C., more preferably at 20°–60° C.

This reaction should preferably be carried out in the presence of a solvent. Examples of the solvent follow: alcohol type solvents including methanol, ether type solvents including tetrahydrofuran, dioxane and ethyleneglycoldimethyl ether, hydrocarbon type solvents including benzene, xylene, n-hexane and cyclohexane, and nitrile type solvents including acetonitrile. The solvent is not limited to these examples.

The second step, that is, the reaction between the reaction product of sodium hydride anhydride and hydrogen sulfide and 3-halopropylalkoxy silane, is described below.

The amount of 3-halopropylalkoxy silane is theoretically 2 equivalents of sodium sulfide anhydride. However, preferably 1.5–2.5 equivalents, more preferably 1.6–1.9 equivalents is added to completely consume the raw material 3-halopropylalkoxy silane which is hard to separate from the product by means of distillation. The reaction is carried out preferably at 20°–100° C., more preferably at 60°–80° C.

When carrying out this reaction, it is preferable to pressure-feed 3-halopropylalkoxy silane under airtight conditions or drip 3-halopropylalkoxy silane under a hydrogen sulfide gas flow.

[The reaction between hydrogensulfide of alkali metal and 3-halopropylalkoxy silane]

This reaction is represented by $$NaOMe + H_2S \rightarrow NaSH + MeOH \qquad (1)$$

and $$NaSH + X(CH_2)_3Si(OR)_aR_{3-a} \rightarrow HS(CH_2)_3Si(OR)_aR_{3-a} + NaX. \qquad (2)$$

Side reactions are represented by $$2 NaOMe + H_2S \rightarrow Na_2S + 2 MeOH \qquad (3)$$

and $$Na_2S + 2X(CH_2)_3Si(OR)_aR_{3-a} \rightarrow S\{(CH_2)_3Si(OR)_aR_{3-a}\} + 2 NaX. \qquad (4)$$

Sodium sulfide generated in the side reaction shown in (3) causes the production of the by-product sulfide through reaction (4). The conditions of the present invention, i.e. the presence of hydrogen sulfide and airtightness, are necessary. When sodium hydrogensulfide is consumed by reaction (2), the following equilibrium reaction (5) proceeds toward the right and the amount of the by-product sodium sulfide decreases, thus suppressing the production of the by-product sulfide.

$$½ Na_2S + ½ H_2S \rightarrow NaSH \qquad (5)$$

On the other hand, it is believed that the method in which hydrogen sulfide is blown in at the time of the reaction (2) in the open system results in an insufficient amount of dissolved hydrogen sulfide and equilibrium reaction (5) does not proceed toward the right, leaving sodium sulfide which increases the amount of the by-product sulfide.

Details of the aforementioned reaction are described here. This reaction is preferably carried out in the presence of a solvent. Examples of solvents which can be used include, but are not limited to, those listed for said reaction using sodium sulfide anhydride. Usually, this reaction is carried out using an alcohol solvent such as methanol or ethanol.

Examples of the hydrogensulfide of alkali metal used in this reaction include sodium hydrogensulfide and potassium hydrogensulfide, and sodium hydrogensulfide is particularly preferable sodium hydrogensulfide can be prepared outside of the system, but usually sodium hydrogensulfide is synthesized by injecting hydrogen sulfide into the alcohol solution of sodium alcholate in the system.

In the present invention, more hydrogen sulfide is forcefully injected into this solution so that an excess amount of hydrogen sulfide is present in the system. This injection should be carried out gradually because it takes some time for hydrogen sulfide to dissolve in the alcohol solution of sodium hydrogensulfide. The pressure in the system increases gradually and from here on the process proceeds under pressurized conditions.

Specifically, when the concentration of the methanol solution of sodium methylate is 24–28%, 1.1–2.0 moles, preferably 1.1–1.5 moles, more preferably 1.3–1.5 moles, of hydrogen sulfide for 1 mole of sodium methylate is injected at atmospheric pressure at the start and later forcibly injected under pressure. The temperature at this time is preferably 50° C. or lower. If it is 30° C. or lower, then injection can be carried out at 2 $kg_f/cm^2$ or lower, a pressure relatively easy to handle. Therefore, the injection of hydrogen sulfide must be carried out with a pressure proof apparatus. The injection time is usually approximately 1 hour from when sodium hydrogensulfide is generated and injection of excess hydrogen sulfide begins. However, the time can be shortened if the injection pressure is increased. If injection of hydrogen sulfide is carried out in two stages because of reasons related to handling of the manufacturing apparatus, then, by adjusting the amount of hydrogen sulfide to 1.1 moles or less for 1 mole of sodium methylate in the first step injection, it is possible to eliminate the need for pressure proofing in the first step manufacturing apparatus for sodium hydrogensulfide.

The amount of sodium hydrogensulfide is 1.03–1.20 moles, preferably 1.03–1.05 moles, for 1 mole of 3-chloropropyltrialkoxy silane to be reacted. The concentration of hydrogen sulfide in the system should be preferably 0.1–1.0 moles, more preferably 0.1–0.5 moles, for 1 mole of this sodium hydrogensulfide. The hydrogen sulfide can all be injected before adding the 3-chloropropyltrialkoxy silane, or the injection can be divided between before and after the reaction.

The alcohol solution of sodium hydrogensulfide prepared by dissolving hydrogen sulfide is then heated up to preferably 50°–100° C., more preferably 65°–100° C., under airtight conditions. The pressure at this time will be 2.0–5.0 kg/cm². 3-chloropropyltrialkoxy silane is then gradually dripped into it. The dripping of 3-chloropropyltrialkoxy silane into sodium hydrogensulfide is advantageous for the suppression of production of by-product sulfide.

Also, choosing a drip time of 1 hour or longer, preferably 1–3 hours, similarly suppresses the production of by-product sulfide. However, a dripping time longer than 3 hours does not result in a significant improvement over 3 hours.

When 3-chloropropyltrialkoxy silane is dripped into sodium hydrogensulfide, the system pressure gradually decreases. Pressure injection of hydrogen sulfide to keep the pressure preferably at 1.0–4.0 kg/cm², more preferably at 2.0–4.0 kg/cm², gives a desirable result. It is also possible to set the pressure of hydrogen sulfide a little higher at the start of the reaction so that the pressure will be in this range after reduction of the pressure due to the reaction.

The higher the temperature, the shorter the time required for aging of the solution after completion of the dripping. 70° C. or higher is adequate for the aging temperature, but 90° C.–120° C. is preferable. If the temperature is 70° C. or lower, then the aging takes 5 hours or longer. If the temperature is 120° C. or higher, then the pressure load on the apparatus becomes significant.

What is characteristic of the present invention is the fact that hydrogen sulfide, which is believed to be unnecessary for the essential reaction, is introduced into the system. This operation has an effect of suppressing the production of sulfide down to about 1%, whereas conventionally 5–10% sulfide production has been deemed unavoidable. Also, since the reaction is carried out under airtight conditions, polymers which would otherwise be generated through hydrolysis due to moisture penetration from the atmosphere are not generated, resulting in a high yield.

The present invention is superior to the prior art methods for the following reasons:
(1) The reaction yield of the present invention is superior to that of the prior art methods. Also, production of by-products which contain hazardous components are significantly reduced to reduce the load of waste treatment and such.
(2) The reaction apparatus is simple. Also, since the solvent is methanol which is easy to recover, the load of the after treatment for purification is reduced.
(3) The time required from when hydrogen sulfide injection into sodium hydrogensulfide begins to when the reaction is completed is short, making the present invention practical as an industrial manufacturing method.

EXAMPLES

The present invention is described in detail below by referring to examples. The present invention is not limited to these examples.

[Example 1]

93.6 g (1.2 mole) of sodium sulfide anhydride was put into a 1-liter 4-mouth flask equipped with a stirrer, a reflux condenser, a thermometer and a gas blow-in tube(s). 400 g of methanol was added to dissolve the sodium sulfide anhydride. At this time, the internal temperature rose to approximately 60° C. due to the heat generation. After the dissolution was complete, 53.2 g (1.56 mol) of hydrogen sulfide was blown into the system for 2 hours at 30°–40° C.

The reaction solution was then put into a 1-liter autoclave and heated until the internal temperature reached 70° C. At this time, the internal pressure reached 1 kg/cm². 397.4 g (2.0 mol) of 3-chloropropyltrimethoxy silane was pressure-fed into this for 1 hour and the reaction was carried out at 70°–80° C. After completion of the pressure-feeding of 3-chloropropyltrimethoxy silane, the temperature was kept at 70°–80° C. for 4 hours for aging.

This reaction solution was cooled and sodium chloride was removed by means of filtering. At this time, the filtrate was analyzed using gas chromatography. As shown in the product ratio below, the amount of sulfide produced was very small.

| | |
|---|---|
| $HS(CH_2)_3Si(OMe)_3$ | 97.7% |
| $S\{(CH_2)_3Si(OMe)_3\}_2$ | 2.3% |

After methanol was distilled away from the filtrate, vacuum distillation was carried out. 344.7 g of 3-mercaptopropyltrimethoxy silane was obtained as a cut with a boiling point of 85° C. at a pressure of 4 mmHg. The yield was 87.8%

[Example 2]

93.6 g (1.2 mole) of sodium sulfide anhydride was put into a 1-liter 4-mouth flask equipped with a stirrer, a reflux condenser, a thermometer, a gas blow-in tube(s) and a dripping funnel. 400 g of methanol was added to dissolve the sodium sulfide anhydride. After the dissolution was complete, 53.2 g (1.56 mol) of hydrogen sulfide was blown into the system for 2 hours at 30°–40° C.

After the internal temperature was heated up to 70° C., 397.4 g (2.0 mol) of 3-chloropropyltrimethoxy silane was dripped through the dripping funnel and simultaneously 7.2 g (0.21 mol) of hydrogen sulfide was blown-in. The reaction was carried out for 1 hour at 65°–75° C.

After completion of the dripping and the blowing-in, the temperature was kept at 60°–70° C. for 5 hours for aging. This reaction solution was cooled and sodium chloride was removed by means of filtering. At this time, the filtrate was analyzed using gas chromatography. As shown in the product ratio below, the amount of sulfide produced was small.

| | |
|---|---|
| $HS(CH_2)_3Si(OMe)_3$ | 92.9 |
| $S\{(CH_2)_3Si(OMe)_3\}_2$ | 7.1 |

After methanol was distilled away from the filtrate, vacuum distillation was carried out. 313.7 g of 3-mercaptopropyltrimethoxy silane was obtained. The yield was 79.9%.

[Example 3]

351 g of 3-mercaptopropyltrimethoxy silane was obtained in the same manner as in Example 1 except for the fact that 485.8 g (2.0 mol) of 3-bromopropyltrimethoxy silane was used instead of the 3-chloropropyltrimethoxy silane in Example 1. The yield was 89.4%.

[Example 4]

462.9 g of a methanol solution of 28% sodium methoxide (2.4 mol) was put into a 1-liter 4-mouth flask equipped with a stirrer, a reflux condenser, a thermometer and a gas blow-in tube(s) and 88.5 g (2.60 mol) of hydrogen sulfide was blown into the system for 4 hours at 30°–40° C.

The reaction solution was then put into a 1-liter autoclave and heated until the internal temperature reached 70° C. At this time, the internal pressure reached 1 kg/cm$^2$. 397.4 g (2.0 mol) of 3-chloropropyltrimethoxy silane was pressure-fed into this for 1 hour and the reaction was carried out at 70°–80° C. After completion of the pressure-feeding of the 3-chloropropyltrimethoxy silane, the temperature was kept at 70°–80° C. for 3 hours for aging.

This reaction solution was cooled and sodium chloride was removed by means of filtering. At this time, the filtrate was analyzed using gas chromatography. As shown in the product ratio below, the amount of sulfide produced was very small.

| | |
|---|---|
| HS(CH$_2$)$_3$Si(OMe)$_3$ | 97.6% |
| S{(CH$_2$)$_3$Si(OMe)$_3$}$_2$ | 2.4% |

After methanol was distilled away from the filtrate, vacuum distillation was carried out. 327.8 g of 3-mercaptopropyltrimethoxy silane was obtained as a cut with a boiling point of 85° C. at a pressure of 4 mmHg. The yield was 83.5%.

[Example 5]

303.8 g of a methanol solution of 28% sodium methoxide (1.58 mol) was put into a 1-liter 4-mouth flask equipped with a stirrer, a reflux condenser, a thermometer and a gas blow-in tube(s) and 57.3 g (1.68 mol) of hydrogen sulfide was blown into the system for 2 hours at 30°–40° C.

The internal temperature was heated up to 70° C. At this time, the internal pressure reached 1.5 kg,/cm$^2$. 298.1 g (1.50 mol) of 3-chloropropyltrimethoxy silane was pressure-fed into this for 1 hour and the reaction was carried out at 70°–80° C. After completion of the pressure-feeding of the 3-chloropropyltrimethoxy silane, the temperature was kept at 100° C. for 1 hour for aging.

This reaction solution was cooled and sodium chloride was removed by means of filtering. At this time, the filtrate was analyzed using gas chromatography. As shown in the product ratio below, the amount of sulfide produced was very small.

| | |
|---|---|
| HS(CH$_2$)$_3$Si(OMe)$_3$ | 97.2% |
| S{(CH$_2$)$_3$Si(OMe)$_3$}$_2$ | 2.8% |

After methanol was distilled away from the filtrate, vacuum distillation was carried out. 255.9 g of 3-mercaptopropyltrimethoxy silane was obtained as a cut with a boiling point of 85° C. at a pressure of 4 mmHg. The yield was 86.9%.

[Example 6]

342.3 g of 3-mercaptopropyltrimethoxy silane was obtained in the same manner as in Example 1 except for the fact that 485.8 g (2.0 mol) of 3-bromopropyltrimethoxy silane was used instead of the 3-chloropropyltrimethoxy silane in Example 4. The yield was 87.2%.

[Comparative Example 1]

462.9 g of a methanol solution of 28% sodium methoxide (2.4 mol) was put into a 1-liter 4-mouth flask equipped with a stirrer, a reflux condenser, a thermometer and a gas blow-in tube(s) and 92.2 g (2.71 mol) of hydrogen sulfide was blown into the system for 3 hours at 30°–40° C.

After the internal temperature was heated up to 70° C., 397.4 g (2.0 mol) of 3-chloropropyltrimethoxy silane was dripped through the dripping funnel, and the reaction was carried out for 1 hour at 65°–75° C. After completion of the dripping, the temperature was kept at 60°–70° C. for 3 hours for aging. This reaction solution was cooled and sodium chloride was removed by means of filtering. At this time, the filtrate was analyzed using gas chromatography. As shown in the product ratio below, a large amount of sulfide was produced.

| | |
|---|---|
| HS(CH$_2$)$_3$Si(OMe)$_3$ | 50.1% |
| S{(CH$_2$)$_3$Si(OMe)$_3$}$_2$ | 49.9% |

[Comparative Example 2]

462.9 g of a methanol solution of 28% sodium methoxide (2.4 mol) was put into a 1-liter 4-mouth flask equipped with a stirrer, a reflux condenser, a thermometer and a gas blow-in tube(s) and 95.8 g (2.81 mol) of hydrogen sulfide was blown into the system for 3 hours at 30°–40° C.

After the internal temperature was heated up to 70° C., 397.4 g (2.0 mol) of 3-chloropropyltrimethoxy silane was dripped through the dripping funnel and simultaneously 48.4 g (1.42 mol) of hydrogen sulfide was blown-in. The reaction was carried out for 1 hour at 65°–75° C. After completion of the dripping and the blowing-in, the temperature was kept at 60°–70° C. for 3 hours for aging.

This reaction solution was cooled and sodium chloride was removed by means of filtering. At this time, the filtrate was analyzed using gas chromatography. As shown in the product ratio below, a large amount of sulfide was produced.

| | |
|---|---|
| HS(CH$_2$)$_3$Si(OMe)$_3$ | 81.7% |
| S{(CH$_2$)$_3$Si(OMe)$_3$}$_2$ | 18.3% |

[Example 7]

267.6 g of a methanol solution of 22% sodium hydrogen-sulfide anhydride (1.05 mol) was put into an autoclave with an internal volume of 1 liter, and the air was replaced by nitrogen. 0.3 mol of hydrogen sulfide was then blown in and the system was pressurized to 0.9 kgf/cm$^2$ to oversaturate hydrogen sulfide. After heating the system up to 70° C., 198.7 g (1.0 mole) of 3-chloropropyltrimethoxy silane was dripped for 3 hours, and, during the dripping, 0.05 mol of hydrogen sulfide was blown into the system so that the pressure in the system was kept at 2.5 kgf/cm$^2$. After the dripping, the temperature was raised to 100° C. and the system was aged for 1 hour, followed by cooling. By-product salts produced in the reaction were filtered away. The composition was analyzed by means of gas chromatography. 3-mercaptopropyltrimethoxy silane was obtained with a yield of 94.1%.

[Example 8]

267.6 g of a methanol solution of 22% sodium hydrogen-sulfide anhydride (1.05 mol) was put into an autoclave with an internal volume of 1 liter and the air was replaced by nitrogen. 0.3 mol of hydrogen sulfide was then blown in and the system was pressurized to 0.9 kgf/cm$^2$ to oversaturate hydrogen sulfide. After heating the system up to 90° C., 198.7 g (1.0 mole) of 3-chloropropyltrimethoxy silane was dripped for 3 hours, and during the dripping, 0.1 mol of hydrogen sulfide was blown into the system so that the pressure in the system was kept at 3.5 kgf/cm². After the dripping, the system was aged for 2 hour at 90° C., followed by cooling. By-product salts produced in the reaction were filtered away. The composition was analyzed by means of gas chromatography. 3-mercaptopropyltrimethoxy silane was obtained with a yield of 93.5%.

[Comparative Example 3]

267.6 g of a methanol solution of 22% sodium hydrogensulfide anhydride (1.05 mol) was put into an autoclave with an internal volume of 1 liter and the air was replaced by nitrogen. After heating the system up to 70° C., 198.7 g (1.0 mole) of 3-chloropropyltrimethoxy silane was injected. The system was aged for 4 hours at 70° C., and cooled after the 3-chloropropyltrimethoxy silane disappeared. The pressure in the system during aging was 0.7–0.9 kgf/cm². By-product salts produced in the reaction were filtered away. The composition was analyzed by means of gas chromatography. 3-mercaptopropyltrimethoxy silane was obtained with a yield of 81.0%.

[Comparative Example 4]

308 g of a dimethylformamide solution of 20% sodium hydrogensulfide anhydride (1.1 mol) was put into an autoclave with an internal volume of 1 liter and the air was replaced by nitrogen. After heating the system up to 110° C., 198.7 g (1.0 mole) of 3-chloropropyltrimethoxy silane was injected. The system was aged for 2 hours at 110° C., and cooled after the 3-chloropropyltrimethoxy silane disappeared. By-product salts produced in the reaction were filtered away. The composition was analyzed by means of gas chromatography. 3-mercaptopropyltrimethoxy silane was obtained with a yield of 83.6%.

[Comparative example 5]

267.6 g of a methanol solution of 22% sodium hydrogensulfide anhydride (1.05 mol) was put into an autoclave with an internal volume of 1 liter and the air was replaced by nitrogen. 198.7 g (1.0 mole) of 3-chloropropyltrimethoxy silane was injected and the system was aged for 4 days at room temperature until the 3-chloropropyltrimethoxy silane disappeared. By-product salts produced in the reaction were filtered away. The composition was analyzed by means of gas chromatography. 3-mercaptopropyltrimethoxy silane was obtained with a yield of 40.3%.

What is claimed is:

1. A method of manufacturing 3-mercaptopropylalkoxy silane wherein 3-halopropylalkoxy silane represented by the general formula $$X(CH_2)_3Si(OR)_aR_{3-a} \qquad (I)$$

is reacted in the reaction product obtained by reacting sodium sulfide anhydride and hydrogen sulfide, wherein X denotes Cl or Br; R denotes a methyl, ethyl or propyl group wherein R's can be all identical or different from each other; and "a" denotes an integer 1, 2 or 3.

2. A method of manufacturing 3-mercaptopropylalkoxy silane wherein a hydrogensulfide of alkali metal and 3-halopropylalkoxy silane represented by the general formula $$X(CH_2)_3Si(OR)_aR_{3-a} \qquad (I)$$

are reacted under airtight and pressurized conditions in the presence of hydrogen sulfide, wherein X denotes Cl or Br; R denotes a methyl, ethyl or propyl group wherein R's can be all identical or different from each other; and "a" denotes an integer 1, 2 or 3.

3. A method of claim 2 wherein 0.1–1.0 moles of hydrogen sulfide is used for 1 mole of the hydrogensulfide of alkali metal.

4. A method of claim 2 wherein the pressure in the system is 0.5–4.0 kg/cm² at room temperature.

5. A method of claim 2 wherein an alcohol solution of a hydrogensulfide of alkali metal pressurized with hydrogen sulfide is heated up to 50°–100° C., followed by dripping of 3-chloropropyltrialkoxy silane.

6. A method of claim 1 wherein the 3-halopropylalkoxy silane is 3-halopropyltrimethoxy silane.

7. A method of claim 2 wherein the hydrogensulfide of alkali metal is obtained by reacting sodium methoxide and a stoichiometric excess amount of hydrogen sulfide.

* * * * *